United States Patent
Okochi et al.

(10) Patent No.: US 8,632,808 B2
(45) Date of Patent: Jan. 21, 2014

(54) TASTE-MASKING SOLID PREPARATION OF PIOGLITAZONE

(75) Inventors: Kazuhiro Okochi, Osaka (JP); Arisa Maeda, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 489 days.

(21) Appl. No.: 12/298,418

(22) PCT Filed: Apr. 26, 2007

(86) PCT No.: PCT/JP2007/059430
§ 371 (c)(1),
(2), (4) Date: Oct. 24, 2008

(87) PCT Pub. No.: WO2007/126136
PCT Pub. Date: Nov. 8, 2007

(65) Prior Publication Data
US 2010/0034891 A1    Feb. 11, 2010

(30) Foreign Application Priority Data

Apr. 27, 2006 (JP) ................................. 2006-124456

(51) Int. Cl.
*A61K 9/32* (2006.01)
*A61K 9/14* (2006.01)
*A61K 31/425* (2006.01)

(52) U.S. Cl.
USPC ........... 424/482; 424/464; 424/474; 424/475; 424/489; 514/369

(58) Field of Classification Search
None
See application file for complete search history.

(56) References Cited

U.S. PATENT DOCUMENTS

| 4,708,867 A | 11/1987 | Hsiao |
| 5,972,373 A | 10/1999 | Yajima et al. |
| 7,399,485 B1 | 7/2008 | Shimizu et al. |
| 2004/0033258 A1 | 2/2004 | Koike |
| 2006/0141023 A1* | 6/2006 | Trehan et al. ................. 424/451 |
| 2006/0182796 A1 | 8/2006 | Wu et al. |
| 2006/0182802 A1 | 8/2006 | Shimizu et al. |
| 2006/0286168 A1 | 12/2006 | Koike et al. |

FOREIGN PATENT DOCUMENTS

| EP | 1329217 A1 * | 7/2003 |
| JP | 2001-192344 A | 7/2001 |
| WO | WO 00/06126 A1 | 2/2000 |
| WO | WO 02/30400 A1 | 4/2002 |
| WO | WO 2004/006921 A1 | 1/2004 |

OTHER PUBLICATIONS

International Search Report dated Sep. 9, 2008, from corresponding PCT/JP2007/059430, 4 pages.
Written Opinion of the International Searching Authority from corresponding PCT/JP2007/059430, 7 pages, Feb. 18, 2009.
Nanda et al., "An Update on Taste Masking Technologies for Oral Pharmaceuticals," Indian J. Pharm. Sci., 2002, 64(1):10-17, XP008043034.
Reo et al., "Taste Masking Science and Technology Applied to Compacted Oral Solid Dosage Forms—Part 2," American Pharmaceutical Review, Jan. 1, 2002, 5(3):8-23, XP001118960.
Toshio et al., "Eudragit E. Anwendung in der Arzneimittelherstellung," Röhm Pharma Announcement, Jan. 1, 1979, 1-8, XP002045877.

* cited by examiner

*Primary Examiner* — Lakshmi Channavajjala
(74) *Attorney, Agent, or Firm* — Foley & Lardner LLP

(57) ABSTRACT

A solid preparation sufficiently masking the unpleasant taste of pioglitazone or a salt thereof; a solid preparation sufficiently masking the unpleasant taste of pioglitazone or a salt thereof and having superior properties of superior disintegration property in the oral cavity, appropriate preparation strength, long-term preservation stability and the like is provided. The present invention provides a solid preparation comprising particles comprising (i) core particles comprising an excipient, and (ii) pioglitazone or a salt thereof and an acid-soluble polymer both coating the core particles.

10 Claims, No Drawings

TASTE-MASKING SOLID PREPARATION OF PIOGLITAZONE

TECHNICAL FIELD

The present invention relates to a solid preparation comprising particles comprising (i) core particles comprising an excipient, and (ii) pioglitazone or a salt thereof and an acid-soluble polymer both coating the core particles.

BACKGROUND OF THE INVENTION

As a preparation masking the unpleasant taste of pioglitazone or a salt thereof, the following preparation has been reported. A solid preparation containing 1) a basic medicinal component having an unpleasant taste, 2) a saccharide, 3) a polyanionic polymer, 4) a corrigent and 5) carboxymethylcellulose (patent reference 1: WO02/30400).

DISCLOSURE OF THE INVENTION

For a pharmaceutical product with high administration compliance for patients, the development of a solid preparation sufficiently masking the unpleasant taste of pioglitazone or a salt thereof has been desired.

Moreover, the development of a solid preparation sufficiently masking the unpleasant taste of pioglitazone or a salt thereof and having superior properties of good disintegration property in the oral cavity, appropriate preparation strength, long-term preservation stability and the like has been desired.

The present inventors have studied formulation of pioglitazone or a salt thereof having an unpleasant taste, and found that a solid preparation sufficiently masking the unpleasant taste of pioglitazone or a salt thereof can be obtained by the use of pioglitazone or a salt thereof and an acid-soluble polymer in combination and coating core particles comprising an excipient with pioglitazone or a salt thereof and an acid-soluble polymer.

Accordingly, the present invention provides the following.
1) A solid preparation comprising particles comprising (i) core particles comprising an excipient, and (ii) pioglitazone or a salt thereof and an acid-soluble polymer both coating the core particles (hereinafter sometimes to be abbreviated as the solid preparation of the present invention).
2) The preparation of the aforementioned 1), wherein the acid-soluble polymer is aminoalkylmethacrylate copolymer E or polyvinylacetal diethylaminoacetate.
3) The preparation of the aforementioned 1), wherein the pioglitazone or a salt thereof is pioglitazone hydrochloride.
4) The preparation of the aforementioned 1), which is a solid preparation rapidly disintegrating in the oral cavity.
5) The preparation of the aforementioned 1), comprising particles wherein the core particles comprising an excipient are coated with (i) a coating layer comprising the pioglitazone or a salt thereof, and (ii) a coating layer comprising the acid-soluble polymer, wherein said coating layer (ii) is formed on said coating layer (i).
6) The preparation of the aforementioned 1), comprising particles wherein the core particles comprising an excipient are coated with a coating layer comprising the pioglitazone or a salt thereof and the acid-soluble polymer.
7) The preparation of the aforementioned 1), further comprising a saccharide preferably in a part other than the core particles.
8) The preparation of the aforementioned 1), further comprising a disintegrant preferably in a part other than the core particles.
9) The preparation of the aforementioned 1), further comprising crystalline cellulose preferably in a part other than the core particles.
10) The preparation of the aforementioned 1), further comprising a sweetener preferably in a part other than the core particles.

EFFECT OF THE INVENTION

The solid preparation of the present invention can be administered very easily since the unpleasant taste of pioglitazone and a salt thereof is sufficiently masked, and therefore, is useful as a pharmaceutical product with high administration compliance for patients. When the solid preparation of the present invention is a solid preparation rapidly disintegrating in the oral cavity, the solid preparation is extremely useful as a pharmaceutical product with high administration compliance for patients having difficulty in swallowing pharmaceutical agents, such as the elderly and children, and the like, since the unpleasant taste of pioglitazone and a salt thereof is sufficiently masked and the preparation has superior disintegration property in the oral cavity. Moreover, the solid preparation rapidly disintegrating in the oral cavity shows superior properties of appropriate preparation strength, long-term preservation stability and the like.

The present invention is explained in detail in the following.

As the "core particles comprising an excipient" to be used for the solid preparation of the present invention, one or two kinds selected from lactose, crystalline cellulose, sucrose, cornstarch, D-mannitol and the like can be mentioned. The "core particles comprising an excipient" means particles having an almost uniform shape and size afforded by spray-drying or granulation by a wet granulation method, a dry granulation method or a heat granulation method. As the shape, a spherical shape is preferable.

The particle size (particle distribution range) of the core particle is preferably 50-500 μm, more preferably 100-300 μm.

The particle size is measured, for example, using a laser diffraction particle distribution apparatus (e.g., SYNPATEC HELOS-RODOS particle distribution apparatus).

Specific examples of the core particle include lactose-crystalline cellulose spherical granule [trade name: Nonpareil 105 (particle distribution range: 180-300 μm), Nonpareil 105T (particle distribution range: 105-255 μm); manufactured by Freund Corporation], crystalline cellulose spherical core particle [trade name: CELPHERE SCP-100 (particle distribution range: 75-212 μm), CELPHERE CP-203 (particle distribution range: 150-300 μm), CELPHERE CP-305 (particle distribution range: 300-500 μm); manufactured by Asahi Kasei Chemicals Corporation], sucrose-starch spherical core particle [trade name: Nonpareil 101, manufactured by Freund Corporation], refined sucrose spherical core particle [trade name: Nonpareil 103, manufactured by Freund Corporation], D-mannitol spherical core particle [trade name: Nonpareil 108 grade 200 (particle distribution range: 150-250 μm), Nonpareil 108 grade 32-42 (particle distribution range: 355-500 μm), manufactured by Freund Corporation], lactose granulated powder [trade name: dylactose R, dylactose S, manufactured by Freund Corporation], lactose for direct tableting [trade name: SUPER-TAB, manufactured by Asahi Kasei Chemicals Corporation]. Of these, lactose-crystalline cellulose spherical granule is preferable, and Nonpareil 105T (trade name, particle distribution range: 105-255 μm) is further preferable.

The content of the "core particles comprising an excipient" in the solid preparation of the present invention is generally 1-50 parts by weight, preferably 5-25 parts by weight, per 100 parts by weight of the solid preparation.

Pioglitazone and a salt thereof to be used for the solid preparation of the present invention have an unpleasant taste (e.g., bitter taste, hot taste, pungent taste).

As the salt of pioglitazone, pharmacologically acceptable salts, for example, salts with inorganic acid, salts with organic acid, salts with acidic amino acid and the like can be mentioned.

Preferable examples of the salts with inorganic acid include salts with hydrochloric acid, hydrobromic acid, nitric acid, sulfuric acid, phosphoric acid and the like.

Preferable examples of the salts with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salts with acidic amino acid include salts with aspartic acid, glutamic acid and the like.

Pioglitazone and a salt thereof may be diluted with a diluent and the like that are generally used for medical field, food field and the like.

Pioglitazone or a salt thereof is preferably pioglitazone hydrochloride.

While the content of pioglitazone or a salt thereof in the solid preparation of the present invention varies depending on the dose and the like, it is generally 0.01-40 parts by weight, preferably 1-20 parts by weight, more preferably 5-10 parts by weight, per 100 parts by weight of the solid preparation.

The "acid-soluble polymer" to be used for the solid preparation of the present invention refers to a polymer that dissolves in an acidic aqueous solution at pH 5.8 or below. As the "acid-soluble polymer", for example, aminoalkylmethacrylate copolymer E (trade name: Eudragit E, Eudragit E 100, Eudragit E PO, Eudragit E 12,5), polyvinylacetal diethylaminoacetate (trade name: AEA "Sankyo") and the like can be mentioned.

The "acid-soluble polymer" is preferably aminoalkyl methacrylate copolymer E (trade name: Eudragit E 100, Eudragit E PO).

While the content of the acid-soluble polymer in the solid preparation of the present invention varies depending on the kind and the like of the acid-soluble polymer, it is generally 0.1-10 parts by weight, preferably 0.5-5 parts by weight, per 100 parts by weight of the solid preparation.

In the present specification, the "particles" means those having an almost uniform shape and size afforded by granulating a starting material such as powdery, massive, liquid or molten material and the like by a coating method, a wet granulation method, a dry granulation method or a heat granulation method. As the "particles", for example, powder, fine granule and granule can be mentioned. These preferably have the particle size defined in the Japanese Pharmacopoeia 14th Edition.

That is, in a particle size test of a preparation, the particle size of powder is preferably that "the whole amount passes through #18 (850 μm) sieve and not more than 5% of the total amount remains on #30 (500 μm) sieve", the particle size of fine granules is preferably, within the aforementioned range of particle size of powder, that "not more than 10% of the total amount passes through #200 (75 μm) sieve", and the particle size of granule is preferably that "the whole amount passes through #10 (1700 μm) sieve, not more than 5% of the total amount remains on #12 (1400 μm) sieve, and not more than 15% of the total amount passes through #42 (355 μm) sieve".

In the present specification, the average particle size of the "particle" is generally 30-2000 μm, preferably 40-1000 μm. The average particle size is measured, for example, using a laser diffraction particle distribution apparatus (e.g., SYNPATEC HELOS-RODOS particle distribution apparatus).

The "particles" in the present specification may show different shape and size during the preparation process (e.g., compression-molding step) of the solid preparation of the present invention.

The "particles comprising (i) core particles comprising an excipient, and (ii) pioglitazone or a salt thereof and an acid-soluble polymer both coating the core particles" contained in the solid preparation of the present invention (hereinafter sometimes to be abbreviated as the particle of the present invention) only need to be particles wherein the "core particles comprising an excipient" is coated with pioglitazone or a salt thereof and an acid-soluble polymer. As the particles, for example, particles produced by applying or granulating "core particles comprising an excipient", pioglitazone or a salt thereof and an acid-soluble polymer together with, where necessary, the below-mentioned additives; for example, particles produced by applying or granulating "core particles comprising an excipient", pioglitazone or a salt thereof together with, where necessary, the below-mentioned additives, and applying or granulating the obtained coated particles or granulation products and an acid-soluble polymer together with, where necessary, the below-mentioned additives, and the like can be mentioned.

The content of "the particle of the present invention" in the solid preparation of the present invention is, for example, generally 10-100 parts by weight, preferably 15-50 parts by weight, per 100 parts by weight of the solid preparation.

In the present invention, as the main additives, the following saccharides, disintegrant, crystalline cellulose, sweetener and the like can be mentioned.

The solid preparation of the present invention preferably further contains saccharides (preferably in a part other than the core particles).

As the saccharides, for example, sugar, starch sugar, lactose, honey and sugar alcohol can be mentioned. Two or more kinds of these saccharides may be used in a mixture in an appropriate ratio.

As the sugar, for example, sucrose, glycosyl sucrose [coupling sugar (trade name)], fructooligosaccharide and palatinose can be mentioned.

As the starch sugar, for example, glucose, maltose, powdered starch syrup, starch syrup and fructose can be mentioned.

As the lactose, for example, lactose, isomerized lactose (lactulose) and reduction lactose (lactitol) can be mentioned.

As the honey, various kinds of honey generally used for eating can be mentioned.

As the sugar alcohol, for example, sorbitol, D-mannitol, maltitol, hydrogenated glucose syrup, xylitol, reduced paratinose, erythritol and trehalose can be mentioned.

The saccharides are preferably sugar alcohol and lactose, more preferably D-mannitol and lactose.

The content of the saccharides in the solid preparation of the present invention is preferably 10-90 parts by weight, more preferably 40-70 parts by weight, per 100 parts by weight of the solid preparation.

Using 1-20 parts by weight, preferably 2-10 parts by weight, of the saccharides, per 1 part by weight of pioglitazone or a salt thereof, the unpleasant taste of pioglitazone or a salt thereof can be more effectively masked.

The solid preparation of the present invention preferably further contains a disintegrant (preferably in a part other than the core particles).

As the disintegrant, for example, carboxymethylcellulose, calcium carboxymethylcellulose, sodium carboxymethyl starch, croscarmellose sodium, crospovidone, low-substituted hydroxypropylcellulose or hydroxypropyl starch is used.

The disintegrant is preferably crospovidone [preferably Kollidon CL, CL-M, CL-F, CL-SF (trade name, BASF JAPAN LTD.); Polyplasdone XL, XL-10, INF-10 (trade name, ISP JAPAN LTD.)] or low-substituted hydroxypropylcellulose (preferably low-substituted hydroxypropylcellulose having a hydroxypropoxyl group content of 5-16 wt % such as LH11, LH21, LH31, LH22, LH32, LH20, LH30, LH32, LH33 (trade name, manufactured by Shin-Etsu Chemical Co., Ltd.) and the like). Of these, crospovidone is preferable, Kollidon CL, CL-F, CL-SF (trade name, BASF JAPAN LTD.); Polyplasdone XL (trade name, ISP JAPAN LTD.)] are further preferable. By the use of crospovidone, a solid preparation having a superior disintegration property in the oral cavity can be obtained.

The content of the disintegrant in the solid preparation of the present invention is preferably 0.5-25 parts by weight, more preferably 1-15 parts by weight, per 100 parts by weight of the solid preparation.

The solid preparation of the present invention preferably further contains crystalline cellulose (preferably in a part other than the core particles).

As the crystalline cellulose, for example, CEOLUS KG801, KG802, PH101, PH102, PH301, PH302, PH-F20 and RC-A591NF (trade name, manufactured by Asahi Kasei Chemicals Corporation) can be mentioned, including one called microcrystalline cellulose. By the use of crystalline cellulose, a solid preparation having an appropriate preparation strength, and a superior disintegration property in the oral cavity can be obtained.

The content of the crystalline cellulose in the solid preparation of the present invention is preferably 0.1-50 parts by weight, more preferably 0.5-40 parts by weight, further more preferably 1-25 parts by weight, per 100 parts by weight of the solid preparation.

The solid preparation of the present invention preferably further contains a sweetener (preferably in a part other than the core particles).

As the sweetener, for example, aspartame, acesulfame potassium, thaumatin, saccharin sodium and dipotassium glycyrrhizinate can be mentioned. Particularly, aspartame is preferable.

The content of the sweetener in the solid preparation of the present invention is preferably 0.1-15 parts by weight, more preferably 0.2-10 parts by weight, per 100 parts by weight of the solid preparation.

The solid preparation of the present invention may contain, besides the aforementioned saccharides, disintegrant, crystalline cellulose and sweetener, additives conventionally used in the technical field of preparations. As the additive, for example, excipient, binder, lubricant, coloring agent, pH regulator, surfactant, stabilizer, corrigent, flavor, fluidizing agent and the like can be mentioned. These additives are used in an amount conventionally used in the technical field of preparations. Two or more kinds of these additives may be used in a mixture in an appropriate ratio.

As the excipient, for example, starches such as cornstarch, potato starch, wheat starch, rice starch, partly pregelatinized starch, pregelatinized starch, porous starch and the like; anhydrous calcium phosphate, precipitated calcium carbonate, calcium silicate and cellulose powder can be mentioned.

As the binder, for example, hydroxypropylcellulose, hydroxypropylmethylcellulose, povidone (polyvinylpyrrolidone) and gum arabic powder can be mentioned. Of these, hydroxypropylcellulose is preferable.

As the lubricant, for example, magnesium stearate, calcium stearate, talc, sucrose esters of fatty acids and sodium stearyl fumarate can be mentioned. Of these, magnesium stearate is preferable.

As the coloring agent, for example, foodcolors such as Food Yellow No. 5 (Sunset Yellow, same as Food yellow No. 6 in the US), Food Red No. 2, Food Blue No. 2 and the like, food lake colors and yellow ferric oxide can be mentioned.

As the pH regulator, for example, citrate, phosphate, carbonate, tartrate, fumarate, acetate and amino acid salt can be mentioned.

As the surfactant, for example, sodium lauryl sulfate, polysorbate 80, polyoxyethylene (160) polyoxypropylene (30) glycol, polyoxyethylene (196) polyoxypropylene (67) glycol and polyoxyethylene hydrogenated castor oil 60 can be mentioned.

As the stabilizer, for example, sodium ascorbate, tocopherol, tetrasodium edetate, nicotinamide, cyclodextrins; alkaline earth metal salts (e.g., calcium carbonate, calcium hydroxide, magnesium carbonate, magnesium hydroxide, magnesium silicate, magnesium aluminate) and butylhydroxyanisole can be mentioned.

As the corrigent, for example, ascorbic acid, (anhydrous) citric acid, tartaric acid and malic acid can be mentioned.

As the flavor, for example, menthol, peppermint oil, lemon oil and vanillin can be mentioned.

As the fluidizing agent, for example, light anhydrous silicic acid and hydrated silicon dioxide can be mentioned. Here, the light anhydrous silicic acid may be any containing hydrated silicon dioxide ($SiO_2 \cdot nH_2O$) (n is an integer) as a main component and, as concrete examples thereof, Sylysia 320 (trade name, FUJI SILYSIA CHEMICAL LTD.), AEROSIL 200 (trade name, NIPPON AEROSIL CO., LTD.) and the like can be mentioned.

The particle size of the above-mentioned additive is preferably not more than 500 μm that does not easily cause roughness in the oral cavity.

The solid preparation of the present invention is preferably a solid preparation rapidly disintegrating in the oral cavity. Here, the property "rapidly disintegrating in the oral cavity" means disintegration of a solid preparation in the oral cavity in a short time (e.g., 5-90 sec). While the disintegration time in the oral cavity of the solid preparation rapidly disintegrating in the oral cavity (time necessary for a solid preparation to be completely disintegrated with the saliva in the oral cavity of healthy adult male and female) varies depending on the dosage form, size and the like of the solid preparation, when the solid preparation is a tablet, it is, for example, generally about 5-90 sec, preferably 5-60 sec, more preferably 5-30 sec.

The solid preparation rapidly disintegrating in the oral cavity is useful for the prophylaxis or treatment of various diseases as a preparation easily administered to patients having difficulty in swallowing pharmaceutical agents, such as the elderly and children, or a safe preparation for general adults in the time of emergency.

The hardness of the solid preparation of the present invention (measurement value by tablet hardness tester) is about preferably 15-200 N, more preferably 15-150 N.

The solid preparation of the present invention can be produced by coating core particles comprising an excipient with pioglitazone or a salt thereof and an acid-soluble polymer together with, where desired, the aforementioned additives, mixing the obtained coated particles with, where desired, the aforementioned additives, and then compression-molding the mixture.

The "coating", "mixing" and "compression-molding" are performed according to the method conventionally used in the technical field of preparations.

Specifically, the "coating" is performed, for example, using a tumbling fluidized bed granulating-coating machine (MP-10; POWREX CORPORATION) or centrifugal fluidized bed coating granulator (CF-Granulator; Freund Corporation). In addition, "coating" can be performed by granulation using a preparation forming machine such as a high speed agitating granulator (FM-VG-10; POWREX CORPORATION), a fluidized bed granulation dryer (LAB-1, FD-3S, FD-3SN; POWREX CORPORATION) and the like.

The mixing (including granulation, drying, milling and the like) is performed, for example, using a preparation forming machine such as a V-type mixer, a tumbler mixer, a high speed agitating granulator (FM-VG-10; POWREX CORPORATION), an all-round kneader (Hata Tekkosho, Co., Ltd.), a fluidized bed granulation dryer (LAB-1, FD-3S, FD-3SN; POWREX CORPORATION), a box vacuum dryer (Kusunoki Machinery Co., Ltd.), a screen mill (P-3; Showa Kagaku Kikai Kosakusho Co., Ltd.) and the like.

The compression-molding is performed, for example, by punching generally at a pressure of 3-35 kN/cm$^2$ using a single-punch tableting machine (KIKUSUI SEISAKUSHO LTD.), a rotary tableting machine (KIKUSUI SEISAKUSHO LTD.), Auto-graph (Shimadzu Corporation) and the like.

Specific examples of the solid preparation of the present invention include the following preparation (1) and preparation (2).

Preparation (1):

A solid preparation comprising particles wherein core particles comprising an excipient are coated with (i) a coating layer comprising pioglitazone or a salt thereof, and (ii) a coating layer comprising an acid-soluble polymer, wherein said coating layer (ii) is formed on said coating layer (i).

Preparation (2):

A solid preparation comprising particles wherein core particles comprising an excipient are coated with a coating layer comprising pioglitazone or a salt thereof and an acid-soluble polymer.

A layer (intermediate layer) containing a film coating base such as hydroxypropylcellulose, hydroxypropylmethylcellulose, polyvinylpyrrolidone and the like, and further, talc, macrogol and the like may be formed between respective layers.

Of the above-mentioned preparations, preparation (2) can be produced more easily. Further, preparation (2) is more superior in the long-term preservation stability and shows, for example, a smaller time-course difference in the dissolution property of pioglitazone and a salt thereof even after a long-term (e.g., 6 months) preservation. Therefore, preparation (2) is preferable as the solid preparation of the present invention.

Preparation (1) is described in detail in the following.

In preparation (1), the content of the "core particles comprising an excipient" is generally 1-50 parts by weight, preferably 5-25 parts by weight, per 100 parts by weight of the solid preparation.

In preparation (1), the "coating layer comprising pioglitazone or a salt thereof" preferably consists of pioglitazone or a salt thereof, a binder (preferably hydroxypropylcellulose) and a saccharide (preferably lactose). The content of the binder (the binder in the coating layer) in preparation (1) is generally 0.01-50 parts by weight, preferably 0.1-20 parts by weight, per 100 parts by weight of the solid preparation. In addition, the content of the saccharide (the saccharide in the coating layer) in preparation (1) is generally 0.01-50 parts by weight, preferably 0.1-20 parts by weight, per 100 parts by weight of the solid preparation.

In preparation (1), the content of the "coating layer comprising pioglitazone or a salt thereof" is generally 1-50 parts by weight, preferably 5-25 parts by weight, per 100 parts by weight of the solid preparation.

In preparation (1), the "coating layer comprising an acid-soluble polymer" preferably consists of an acid-soluble polymer (e.g., aminoalkylmethacrylate copolymer E), and may further contain an additive selected from polyethylene glycol, talc and (anhydrous) citric acid. The content of the additive (the additive in the coating layer) in preparation (1) is generally 0.01-50 parts by weight, preferably 0.1-20 parts by weight, per 100 parts by weight of the solid preparation.

In preparation (1), the content of the "coating layer comprising an acid-soluble polymer" is generally 0.01-50 parts by weight, preferably 0.1-20 parts by weight, per 100 parts by weight of the solid preparation.

In preparation (1), the content of the "particles wherein core particles comprising an excipient are coated with (i) a coating layer comprising pioglitazone or a salt thereof, and (ii) a coating layer comprising an acid-soluble polymer, wherein said coating layer (ii) is formed on said coating layer (i)" is generally 10-100 parts by weight, preferably 15-50 parts by weight, per 100 parts by weight of the solid preparation.

Preparation (1) preferably further contains, in addition to the above-mentioned "particles wherein core particles comprising an excipient are coated with (i) a coating layer comprising pioglitazone or a salt thereof, and (ii) a coating layer comprising an acid-soluble polymer, wherein said coating layer (ii) is formed on said coating layer (i)", an additive [preferably crystalline cellulose, disintegrant (preferably crospovidone), lubricant (preferably magnesium stearate), saccharides (preferably D-mannitol), coloring agent (preferably yellow ferric oxide), sweetener (preferably aspartame)]. The total content of the additives is generally 1-90 parts by weight, preferably 50-85 parts by weight, per 100 parts by weight of the solid preparation. The content of each single additive is generally 0.001-90 parts by weight, preferably 0.01-85 parts by weight, per 100 parts by weight of the solid preparation.

Preparation (2) is described in detail in the following.

In preparation (2), the content of the "core particles comprising an excipient" is generally 1-50 parts by weight, preferably 5-25 parts by weight, per 100 parts by weight of the solid preparation.

In preparation (2), the "coating layer comprising pioglitazone or a salt thereof and an acid-soluble polymer" preferably consists of pioglitazone or a salt thereof, an acid-soluble polymer (e.g., aminoalkylmethacrylate copolymer E), and a saccharide (preferably lactose). The content of the saccharide (the saccharide in the coating layer) in preparation (2) is generally 0.01-50 parts by weight, preferably 0.1-20 parts by weight, per 100 parts by weight of the solid preparation.

In preparation (2), the content of the "coating layer comprising pioglitazone or a salt thereof and an acid-soluble polymer" is generally 0.01-50 parts by weight, preferably 0.1-20 parts by weight, per 100 parts by weight of the solid preparation.

In preparation (2), the content of the "particles wherein core particles comprising an excipient are coated with a coating layer comprising pioglitazone or a salt thereof and an acid-soluble polymer" is generally 10-100 parts by weight, preferably 15-50 parts by weight, per 100 parts by weight of the solid preparation.

Preparation (2) preferably further contains, in addition to the above-mentioned "particles wherein core particles comprising an excipient are coated with a coating layer comprising pioglitazone or a salt thereof and an acid-soluble polymer", an additive [preferably crystalline cellulose, disintegrant (preferably crospovidone), lubricant (preferably magnesium stearate), saccharides (preferably D-mannitol), coloring agent (preferably yellow ferric oxide), sweetener (preferably aspartame)]. The total content of the additives is generally 1-90 parts by weight, preferably 50-85 parts by weight, per 100 parts by weight of the solid preparation. The content of each single additive is generally 0.001-90 parts by weight, preferably 0.01-85 parts by weight, per 100 parts by weight of the solid preparation.

The production methods of preparation (1) and preparation (2) are described in detail in the following.

Preparation (1) can be produced by coating the core particles comprising an excipient with a coating layer comprising pioglitazone or a salt thereof together with, where desired, the aforementioned additive;
coating the obtained coated particles (a) with a coating layer comprising an acid-soluble polymer together with, where desired, the aforementioned additive;
mixing the obtained coated particles (b) with, where desired, the aforementioned additive; and
compression-molding the mixture.

Preparation (1) can be specifically produced as follows.
(1A) Core particles comprising an excipient (e.g., lactose-crystalline cellulose spherical granule) are granulated with a dispersion of an additive [e.g., binder (e.g., hydroxypropylcellulose), saccharides (e.g., lactose)] and pioglitazone or a salt thereof (preferably pioglitazone hydrochloride) in a solvent (e.g., water);
the obtained granulation products are granulated with a dispersion of an acid-soluble polymer (e.g., aminoalkyl-methacrylate copolymer E) in a solvent (e.g., water-ethanol mixed solvent, aqueous citric anhydride solution, aqueous citric acid monohydrate solution) (the dispersion may contain polyethylene glycol, talc and the like);
the obtained granulation products are mixed with an additive [e.g., crystalline cellulose, disintegrant (e.g., crospovidone), lubricant (e.g., magnesium stearate), saccharides (e.g., D-mannitol), coloring agent (e.g., yellow ferric oxide), sweetener (e.g., aspartame)]; and
the mixture is compression-molded (e.g., tabletted).

Preparation (2) can be produced by coating the core particles comprising an excipient with a coating layer comprising pioglitazone or a salt thereof and an acid-soluble polymer together with, where desired, the aforementioned additive;
mixing the obtained coated particles (c) with, where desired, the aforementioned additive; and
compression-molding the mixture.

Preparation (2) can be specifically produced as follows.
(2A) Core particles comprising an excipient (e.g., lactose-crystalline cellulose spherical granule) are granulated with a dispersion of an additive [e.g., saccharides (e.g., lactose)], pioglitazone or a salt thereof (preferably pioglitazone hydrochloride) and an acid-soluble polymer (e.g., aminoalkyl-methacrylate copolymer E) in a solvent (e.g., water-ethanol mixed solvent, aqueous citric anhydride solution);
the obtained granulation products are mixed with an additive [e.g., crystalline cellulose, disintegrant (e.g., crospovidone), lubricant (e.g., magnesium stearate), saccharides (e.g., D-mannitol), coloring agent (e.g., yellow ferric oxide) and sweetener (e.g., aspartame)]; and
the mixture is compression-molded (e.g., tabletted).

As the dosage form of the solid preparation of the present invention, for example, oral preparations such as tablet, capsule, powder, granule, troche and the like can be mentioned. Of these, tablet is preferable.

The shape of the solid preparation of the present invention is not particularly limited, and may be any of round, caplet, doughnut, oblong and the like.

The solid preparation of the present invention may be coated with a coating agent, and may have a mark and letters for identification and further a score line for partition.

As the coating base, for example, sugar coating base, water-soluble film coating base, enteric film coating base, sustained-release film coating base and the like can be mentioned.

As the sugar coating base, sucrose is used and one or more kinds selected from talc, precipitated calcium carbonate, gelatin, gum arabic, pullulan, carnauba wax and the like may be used in combination.

As the water-soluble film coating base, for example, cellulose polymers such as hydroxypropylcellulose, hydroxypropylmethylcellulose, hydroxyethylcellulose, methylhydroxyethylcellulose and the like; synthetic polymers such as polyvinylacetal diethylaminoacetate, aminoalkyl methacrylate copolymer E [Eudragit E (trade name)], polyvinylpyrrolidone and the like; polysaccharides such as pullulan and the like; and the like can be mentioned.

As the enteric film coating base, for example, cellulose polymers such as hydroxypropylmethylcellulose phthalate, hydroxypropylmethylcellulose acetatesuccinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D55 (trade name)], methacrylic acid copolymer S [Eudragit S (trade name)] and the like; naturally occurring substances such as shellac and the like; and the like can be mentioned.

As the sustained-release film coating base, for example, cellulose polymers such as ethylcellulose, cellulose acetate and the like; acrylic acid polymers such as aminoalkyl methacrylate copolymer RS [Eudragit RS (trade name)], ethyl acrylate-methyl methacrylate copolymer suspension [Eudragit NE (trade name)] and the like; and the like can be mentioned.

Two or more kinds of the above-mentioned coating bases may be used in a mixture in an appropriate ratio. In addition, a coating additive may also be used during coating.

As the coating additive, for example, light masking agents and/or coloring agents such as titanium oxide, talc, ferric oxide and the like; plasticizers such as polyethylene glycol, triethyl citrate, castor oil, polysorbates and the like; organic acids such as citric acid, tartaric acid, malic acid, ascorbic acid and the like; and the like can be mentioned.

The solid preparation of the present invention can be safely administered orally to a mammal (e.g., mouse, rat, rabbit, cat, dog, bovine, horse, monkey, human).

While the dose of the solid preparation of the present invention varies depending on the subject of administration, the kind of the disease and the like, it can be selected from the range affording the effective amount of pioglitazone or a salt thereof.

The dose of the solid preparation of the present invention is, for example, generally 7.5-60 mg/day, preferably 15-60 mg/day, as pioglitazone for one adult (body weight 60 kg), which may be administered in 2-3 portions a day.

When the solid preparation of the present invention is a solid preparation disintegrating in the oral cavity, the solid preparation can be administered without water, or with a suitable amount of water. In addition, the solid preparation can also be administered without disintegration in the oral cavity.

The solid preparation of the present invention is useful, for example, as an agent for the prophylaxis or treatment for the diseases such as diabetes (e.g., type-1 diabetes, type-2 diabetes, gestational diabetes), hyperlipidemia (e.g., hypertriglyceridemia, hypercholesterolemia, hypoHDL-cholesterolemia, postprandial hyperlipidemia), impaired glucose tolerance (IGT), diabetic complications [e.g., neuropathy, nephropathy, retinopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder etc.], obesity, osteoporosis, cachexia (e.g., carcinocachexia, tuberculous cachexia, diabetic cachexia, hemopathic cachexia, endocrinopathic cachexia, infectious cachexia or cachexia induced by acquired immunodeficiency syndrome), fatty liver, hypertension, polycystic ovary syndrome, renal disease (e.g., diabetic nephropathy, glomerulonephritis, glomerulosclerosis, nephrosis syndrome, hypertensive nephrosclerosis, terminal renal disorder), muscular dystrophy, cardiac infarction, angina pectoris, cerebrovascular disorder (e.g., cerebral infarction, cerebral apoplexy), insulin resistance syndrome, Syndrome X, dysmetabolic syndrome, hyperinsulinemia, hyperinsulinemia-induced sensory disorder, tumor (e.g., leukemia, breast cancer, prostate cancer, skin cancer), irritable bowel syndrome, acute or chronic diarrhea, inflammatory disease [e.g., Alzheimer's disease, chronic articular rheumatism, spondylitis deformans, osteoarthritis, lumbago, gout, postoperative or traumatic inflammation, regression of puffiness, neuralgia, pharyngolaryngitis, cystitis, hepatitis (inclusive of nonalcoholic steatohepatitis), pneumonia, pancreatitis, inflammatory colitis, ulcerative colitis], visceral obesity syndrome, arteriosclerosis (e.g., atherosclerosis) and the like; or secondary prevention of the above-mentioned various diseases (e.g., secondary prevention of cardiovascular event such as cardiac infarction and the like) and suppression of progression (e.g., suppression of progression from impaired glucose tolerance to diabetes, suppression of progression to arteriosclerosis in diabetes patients).

The solid preparation of the present invention can be used in combination with an active ingredient other than pioglitazone or a salt thereof (hereinafter sometimes to be abbreviated as concomitant component). In this case, the time of administration of the solid preparation of the present invention and that of the concomitant component are not limited, and they may be administered simultaneously or in a staggered manner to the administration subject. In addition, the solid preparation of the present invention and the concomitant component may be administered to an administration subject as two kinds of preparations each containing the active ingredient, or a single preparation containing the both active ingredients.

The dose of the concomitant component can be appropriately determined based on the dose employed clinically.

Use of the concomitant component in this way provides superior effects such as 1) enhancing the action of the solid preparation of the present invention or the concomitant component (synergistic effect on the action of the pharmaceutical agents), 2) reducing the dose of the solid preparation of the present invention or the concomitant component (effect of reducing the dose of pharmaceutical agents as compared to a single drug administration), 3) reducing the secondary action of the solid preparation of the present invention or the concomitant component, and the like.

As the concomitant component, for example, therapeutic drug for diabetes (excluding insulin sensitizer), therapeutic drug for diabetic complications, therapeutic drug for hyperlipidemia, antihypertensive drug, antiobesity drug, diuretic drug, antithrombotic drug and the like can be mentioned. These active ingredients may be low-molecular-weight compounds, or high-molecular-weight protein, polypeptide, antibody, vaccine and the like. In addition, two or more kinds of the active ingredients may be used in a mixture in an appropriate ratio.

As the therapeutic drug for diabetes, for example, insulin preparations (e.g., animal insulin preparations extracted from the pancreas of bovine, swine; human insulin preparations synthesized by genetic engineering using Escherichia coli or yeast; zinc insulin; protamine zinc insulin; fragment or derivative of insulin (e.g., INS-1)), α-glucosidase inhibitors (e.g., voglibose, acarbose, miglitol, emiglitate), biguanides [e.g., phenformin, metformin, buformin or a salt thereof (e.g., hydrochloride, fumarate, succinate)], insulin secretagogues [e.g., sulfonylurea (e.g., tolbutamide, glibenclamide, gliclazide, chlorpropamide, tolazamide, acetohexamide, glyclopyramide, glimepiride, glipizide, glybuzole), non-sulfonylurea insulin secretagogues (e.g., repaglinide, nateglinide, mitiglinide or calcium salt hydrate thereof)], GLP-1 receptor agonists [e.g., GLP-1, GLP-1MR agent, N,N-2211, exendin-4, BIM-51077, Aib(8,35) hGLP-1 (7,37)$NH_2$, CJC-1131], dipeptidyl-peptidase IV inhibitors (e.g., vildagliptin, saxagliptin, NVP-DPP-278, PT-100, NVP-DPP-728, P32/98, P93/01, TS-021, sitagliptin, denagliptin, T-6666), β3 agonists (e.g., AJ-9677), amylin agonists (e.g., pramlintide), phosphotyrosine phosphatase inhibitors (e.g., sodium vanadate), gluconeogenesis inhibitor (e.g., glycogen phosphorylase inhibitor, glucose-6-phosphatase inhibitor, glucagon antagonist), SGLUT (sodium-glucose cotransporter) inhibitors (e.g., T-1095), 11β-hydroxysteroid dehydrogenase inhibitors (e.g., BVT-3498), adiponectin or agonist thereof, IKK inhibitors (e.g., AS-2868), leptin resistance-improving drug, somatostatin receptor agonists (e.g., compounds described in WO01/25228, WO03/42204, WO98/44921, WO98/45285, WO99/22735), glucokinase activators (e.g., Ro-28-1675) and the like can be mentioned.

As the therapeutic drug for diabetic complications, for example, aldose reductase inhibitors (e.g., tolrestat, epalrestat, zenarestat, zopolrestat, minalrestat, fidarestat, CT-112, ranirestat), neurotrophic factors (e.g., NGF, NT-3, BDNF), neurotrophic factor production-secretion promoters [e.g., neurotrophin production-secretion promoters described in WO01/14372 (e.g., 4-(4-chlorophenyl)-2-(2-methyl-1-imidazolyl)-5-(3-(2-methylphenoxy)propyl)oxazole)], PKC inhibitors (e.g., ruboxistaurin mesylate), AGE inhibitors (e.g., ALT946, pimagedine, pyratoxanthine, N-phenacylthiazolium bromide (ALT766), EXO-226, ALT-711, pyridorin, pyridoxamine), active oxygen scavengers (e.g., thioctic acid), cerebral vasodilators (e.g., tiapuride, mexiletine), somatostatin receptor agonists (e.g., BIM23190) and apoptosis signal regulating kinase-1 (ASK-1) inhibitors can be mentioned.

As the therapeutic drug for hyperlipidemia, for example, HMG-CoA reductase inhibitors (e.g., pravastatin, simvastatin, lovastatin, atorvastatin, fluvastatin, lipantil, itavastatin, rosuvastatin or a salt thereof (e.g., sodium salt, calcium salt)), fibrate compounds (e.g., bezafibrate, beclobrate, binifibrate, ciprofibrate, clinofibrate, clofibrate, clofibric acid, etofibrate, fenofibrate, gemfibrozil, nicofibrate, pirifibrate, ronifibrate, simfibrate, theofibrate), squalene synthase inhibitors (e.g., compounds described in WO97/10224, for example, 1-[[(3R,5S)-1-(3-acetoxy-2,2-dimethylpropyl)-7-chloro-5-(2,3-dimethoxyphenyl)-2-oxo-1,2,3,5-tetrahydro-4,1-benzooxazepin-3-yl]acetyl]piperidine-4-acetic acid), ACAT inhibitors (e.g., avasimibe, eflucimibe), anion exchange resins (e.g., colestyramine), probucol, nicotinic acid drugs (e.g., nicomol, niceritrol), ethyl icosapentate, phytosterol (e.g., soysterol, γ-oryzanol) and the like can be mentioned.

As the antihypertensive drug, for example, angiotensin converting enzyme inhibitors (e.g., captopril, enalapril, delapril), angiotensin II antagonists (e.g., losartan, eprosartan, valsartan, telmisartan, irbesartan, tasosartan, olmesartan medoxomil, 1-[[2'-(2,5-dihydro-5-oxo-4H-1,2,4-oxadiazol-3-yl)biphenyl-4-yl]methyl]-2-ethoxy-1H-benzimidazole-7-carboxylic acid), calcium antagonists (e.g., manidipine, nifedipine, nicardipine, amlodipine, efonidipine), potassium channel openers (e.g., levcromakalim, L-27152, AL0671, NIP-121), clonidine and the like can be mentioned.

As the antiobesity drug, for example, antiobesity drug acting on the central nervous system [e.g., dexfenfluramine, fenfluramine, phentermine, sibutramine, anfepramone, dexamphetamine, mazindol, phenylpropanolamine, clobenzorex; MCH receptor antagonists (e.g., SB-568849; SNAP-7941; compounds described in WO01/82925 and WO01/87834); neuropeptide Y antagonists (e.g., CP-422935); cannabinoid receptor antagonists (e.g., SR-141716, SR-147778); ghrelin antagonist; 11β-hydroxysteroid dehydrogenase inhibitors (e.g., BVT-3498)], pancreatic lipase inhibitors (e.g., orlistat, cetilistat (ATL-962)), β3 agonists (e.g., AJ-9677), anorectic peptides (e.g., leptin, CNTF (ciliary neurotrophic factor)), cholecystokinin agonists (e.g., lintitript, FPL-15849), feeding deterrents (e.g., P-57) and the like can be mentioned.

As the diuretic drug, for example, xanthine derivatives (e.g., theobromine sodium salicylate, theobromine calcium salicylate), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide), antialdosterone preparations (e.g., spironolactone, triamterene), carbonate dehydratase inhibitors (e.g., acetazolamide), chlorobenzenesulfonamide preparations (e.g., chlorthalidone, mefruside, indapamide), azosemide, isosorbide, ethacrynic acid, piretanide, bumetanide, furosemide and the like can be mentioned.

As the antithrombotic drug, for example, heparin (e.g., heparin sodium, heparin calcium, dalteparin sodium), warfarin (e.g., warfarin potassium), anti-thrombin drugs (e.g., aragatroban), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium, sarpogrelate hydrochloride and the like) and the like can be mentioned.

Of the above-mentioned concomitant components, biguanides (preferably metformin), insulin secretagogues (preferably sulfonylurea, non-sulfonylurea insulin secretagogues, more preferably glimepiride, nateglinide, mitiglinide or calcium salt hydrate thereof), HMG-CoA reductase inhibitors (preferably simvastatin), α-glucosidase inhibitors (preferably voglibose) and the like are preferable. When using two or more kinds of concomitant components, the combination of biguanide (preferably metformin) and insulin secretagogue (preferably sulfonylurea, more preferably glimepiride) is preferable.

The present invention further provides "a solid preparation containing pioglitazone or a salt thereof and an acid-soluble polymer". Here, as the "pioglitazone or a salt thereof" and "acid-soluble polymer", those exemplified in the aforementioned solid preparation of the present invention can be used. The solid preparation can be produced in the same manner as in, for example, the aforementioned solid preparation of the present invention, and is useful as a solid preparation suppressing the unpleasant taste of pioglitazone or a salt thereof.

The present invention is explained in detail in the following by referring to Examples, Comparative Examples and Experimental Examples, which are not to be construed as limitative.

In the following Examples and Comparative Examples, as the preparation additives (e.g., lactose, D-mannitol, hydroxypropylcellulose, crospovidone, magnesium stearate, crystalline cellulose), the Japanese Pharmacopoeia 14th Edition or Japanese Pharmaceutical Excipients 2003 compatible products were used.

EXAMPLES

Comparative Example 1

Pioglitazone hydrochloride (694.3 g), hydroxypropylcellulose (189 g, grade SSL, NIPPON SODA CO., LTD.) and lactose (420 g) were measured, dissolved and dispersed in water (3041 g) to give a dispersion.

Lactose-crystalline cellulose spherical granules (1260 g, Nonpareil 105T, Freund Corporation) were charged in a tumbling fluidized bed granulating-coating machine (MP-10, POWREX CORPORATION), and the above-mentioned dispersion was sprayed thereon to give coated particle L.

Coated particle L (6.1 g), sized powder B (12.11 g) obtained in the below-mentioned Example 2, mannitol (0.67 g, mannit S, Towa Chemical Industry Co., Ltd.), mannitol (0.34 g, Cat No: 105980, Merck Ltd., Japan), crystalline cellulose (1.05 g, CEOLUS KG-802, Asahi Kasei Chemicals Corporation), crospovidone (0.53 g, Polyplasdone XL-10, ISP JAPAN LTD.) and magnesium stearate (0.21 g, TAIHEI CHEMICAL INDUSTRIAL CO., LTD.) were measured and mixed.

The obtained mixed powder was tabletted using Autograph (AG-1, Shimadzu Corporation) and 10 $mm_\phi$ punch having a beveled edge at compression pressure 11 ($kN/cm^2$) to give tablets each weighing 420 mg.

Comparative Example 2

Pioglitazone hydrochloride (347.1 g), hydroxypropylcellulose (94.5 g, grade SSL, NIPPON SODA CO., LTD.) and lactose (210 g) were measured, and dissolved and dispersed in water (1521 g) to give a dispersion.

Lactose-crystalline cellulose spherical granules (630 g, Nonpareil 105T, Freund Corporation) were charged in a tumbling fluidized bed granulating-coating machine (MP-10, POWREX CORPORATION), and the above-mentioned dispersion was sprayed thereon to give coated particle M.

Coated particle M (6.1 g), mannitol (13.11 g, Cat No: 105980, Merck Ltd., Japan), crystalline cellulose (1.05 g, CEOLUS KG-802, Asahi Kasei Chemicals Corporation), crospovidone (0.525 g, Polyplasdone XL-10, ISP JAPAN LTD.) and magnesium stearate (0.21 g, TAIHEI CHEMICAL INDUSTRIAL CO., LTD.) were measured and mixed.

The obtained mixed powder was tabletted using Autograph (AG-1, Shimadzu Corporation) and 8 $mm_\phi$ flat punch having a beveled edge at compression pressure 10 ($kN/cm^2$) to give tablets each weighing 210 mg.

Example 1

Coated particle L (500 g) obtained in Comparative Example 1 was charged in a tumbling fluidized bed granulating-coating machine (MP-10, POWREX CORPORATION), and a solution of Eudragit E 100 (81.9 g, aminoalkylmethacrylate copolymer E, Degussa Japan Co., Ltd.) in ethanol (533 g) and water (533 g) was sprayed thereon to give coated particle A.

Separately, mannitol (1635 g, mannit S, Towa Chemical Industry Co., Ltd.) and mannitol (865 g, Cat No: 105980, Merck Ltd., Japan) were charged in a tumbling fluidized bed granulating-coating machine (MP-10, POWREX CORPORATION), and granulated with a dispersion of mannitol (86.5 g, mannit S, Towa Chemical Industry Co., Ltd.) and yellow ferric oxide (1.1 g, Ansted) in water (865.3 g) to give granulation powder B.

Coated particle A (284 g), granulation powder B (464 g), crystalline cellulose (42 g, CEOLUS KG-802, Asahi Kasei Chemicals Corporation), crospovidone (21 g, Polyplasdone XL-10, ISP JAPAN LTD.) and magnesium stearate (8.4 g, TAIHEI CHEMICAL INDUSTRIAL CO., LTD.) were measured and mixed.

The obtained mixed powder was tabletted using Autograph (AG-1, Shimadzu Corporation) and 10 mm$_\phi$ punch having a beveled edge at compression pressure 10 (kN/cm$^2$) to give tablets each weighing 420 mg.

Example 2

Pioglitazone hydrochloride (347 g), Eudragit E PO (42 g, Degussa Japan Co., Ltd.) and lactose (221 g) were measured, and dissolved and dispersed in ethanol (1218 g) and water (987 g) to give a dispersion.

Lactose-crystalline cellulose spherical granules (630 g, Nonpareil 105T, Freund Corporation) were charged in a tumbling fluidized bed granulating-coating machine (MP-10, POWREX CORPORATION), and the above-mentioned dispersion was sprayed thereon to give coated particle C.

Granulation powder B obtained in Example 1 was sized using a power mill (Showa Kagaku Kikai Kosakusho Co., Ltd.) to give sized powder B.

Coated particle C (11.8 g), sized powder B (26.6 g), crystalline cellulose (2.1 g, CEOLUS KG-802, Asahi Kasei Chemicals Corporation), crospovidone (1.1 g, Polyplasdone XL-10, ISP JAPAN LTD.), magnesium stearate (0.4 g, TAIHEI CHEMICAL INDUSTRIAL CO., LTD.) and aspartame (1 g, Ajinomoto Co., Inc.) were measured and mixed.

The obtained mixed powder was tabletted using Autograph (AG-1, Shimadzu Corporation) and 10 mm$_\phi$ punch having a beveled edge at compression pressure 7.5 (kN/cm$^2$) to give tablets each weighing 420 mg.

Example 3

Mannitol (411 g, mannit S, Towa Chemical Industry Co., Ltd.), mannitol (876 g, Cat No: 105980, Merck Ltd., Japan), crystalline cellulose (107.8 g, CEOLUS KG-802, Asahi Kasei Chemicals Corporation), crospovidone (53.9 g, Polyplasdone XL-10, ISP JAPAN LTD.) and aspartame (51.3 g, Ajinomoto Co., Inc.) were charged in a tumbling fluidized bed granulating-coating machine (MP-10, POWREX CORPORATION) and granulated with a dispersion obtained by dissolving and dispersing mannitol (25.7 g, mannit S, Towa Chemical Industry Co., Ltd.) and ferric oxide (2.6 g, manufactured by Ansted) in water (308 g) to give granulation powder D.

Coated particle C (236 g) obtained in Example 2, granulation powder D (596 g) and magnesium stearate (8.4 g, TAIHEI CHEMICAL INDUSTRIAL CO., LTD.) were measured and mixed.

The obtained mixed powder was tabletted using a tabletting machine (Clean Press Correct 19KAWC, KIKUSUI SEISAKUSHO LTD.) and 10 mm$_\phi$ punch having a beveled edge at compression pressure 10 (kN/cm$^2$) to give tablets each weighing 420 mg.

Example 4

Pioglitazone hydrochloride (347 g), hydroxypropylcellulose (94.5 g, grade SSL, NIPPON SODA CO., LTD.) and lactose (220.5 g) were measured, and dissolved and dispersed in water (1545 g) to give a dispersion.

Lactose-crystalline cellulose spherical granules (630 g, Nonpareil 105T, Freund Corporation) were charged in a tumbling fluidized bed granulating-coating machine (MP-10) and the above-mentioned dispersion was sprayed thereon to give coated particle E.

Coated particle E (500 g) was charged in a tumbling fluidized bed granulating-coating machine (MP-10, POWREX CORPORATION), and a solution of Eudragit E PO (40.6 g, Degussa Japan Co., Ltd.) in citric anhydride (13.9 g) and water (218.2 g) was sprayed thereon to give coated particle F.

Coated particle F (13.7 g), mannitol (21.7 g, Cat No:105980, Merck Ltd., Japan), crystalline cellulose (3.15 g, CEOLUS KG-802, Asahi Kasei Chemicals Corporation), crospovidone (2.10 g, Polyplasdone XL-10, ISP JAPAN LTD.), magnesium stearate (0.42 g, TAIHEI CHEMICAL INDUSTRIAL CO., LTD.) and aspartame (1 g, Ajinomoto Co., Inc.) were measured and mixed.

The obtained mixed powder was tabletted using Autograph (AG-1, Shimadzu Corporation) and 10 mm$_\phi$ punch having a beveled edge at compression pressure 10 (kN/cm$^2$) to give tablets each weighing 420 mg.

Example 5

Pioglitazone hydrochloride (347 g), Eudragit E PO (63 g, Degussa Japan Co., Ltd.) and lactose (221 g) were measured, and dissolved and dispersed in ethanol (1218 g) and water (987 g) to give a dispersion.

Lactose-crystalline cellulose spherical granules (630 g, Nonpareil 105T, Freund Corporation) were charged in a tumbling fluidized bed granulating-coating machine (MP-10, POWREX CORPORATION) and the above-mentioned dispersion was sprayed thereon to give coated particle G.

Coated particle G (12 g), mannitol (23.3 g, Cat No: 105980, Merck Ltd., Japan), crystalline cellulose (3.15 g, CEOLUS KG-802, Asahi Kasei Chemicals Corporation), crospovidone (2.1 g, Polyplasdone XL-10, ISP JAPAN LTD.) and magnesium stearate (8.4 g, TAIHEI CHEMICAL INDUSTRIAL CO., LTD.) were measured and mixed.

The obtained mixed powder was tabletted using Autograph (AG-1, Shimadzu Corporation) and 10 mm$_\phi$ punch having a beveled edge at compression pressure 10 (kN/cm$^2$) to give tablets each weighing 420 mg.

The obtained tablets were subjected to a dissolution test at pH 2.0 (KCl/HCl buffer), 900 mL, 50 rpm (Paddle Method), and 97% of pioglitazone hydrochloride was eluted in 15 min.

Example 6

Coated particle L (500 g) obtained in Comparative Example 1 was charged in a tumbling fluidized bed granulating-coating machine (MP-10, POWREX CORPORATION), and a dispersion of Eudragit E 100 (81.9 g, Degussa Japan Co., Ltd.) in ethanol (532.5 g) and water (532.5 g) was sprayed thereon to give coated particle H.

Coated particle H (7.1 g), sized powder B (12.11 g) obtained in Example 2, crystalline cellulose (1.05 g, CEOLUS KG-802, Asahi Kasei Chemicals Corporation), crospovidone (0.53 g, Polyplasdone XL-10, ISP JAPAN LTD.) and magnesium stearate (0.21 g, TAIHEI CHEMICAL INDUSTRIAL CO., LTD.) were measured and mixed.

The obtained mixed powder was tabletted using Auto-graph (AG-1, Shimadzu Corporation) and 10 mm$_\phi$ punch having a beveled edge at compression pressure 11 (kN/cm$^2$) to give tablets each weighing 420 mg.

Example 7

Pioglitazone hydrochloride (347.2 g), Eudragit E PO (94.5 g, Degussa Japan Co., Ltd.) and lactose (220.5 g) were measured and dissolved and dispersed in ethanol (1218 g) and water (987 g) to give a dispersion.

Lactose-crystalline cellulose spherical granules (630 g, Nonpareil 105T, Freund Corporation) were charged in a tumbling fluidized bed granulating-coating machine (MP-10), and the above-mentioned dispersion was sprayed thereon to give coated particle I.

Coated particle I (246.1 g), sized powder B (502.5 g) obtained in Example 2, crystalline cellulose (42.0 g, CEOLUS KG-802, Asahi Kasei Chemicals Corporation), crospovidone (21.0 g, Polyplasdone XL-10, ISP JAPAN LTD.), aspartame (20.0 g, Ajinomoto Co., Inc.) and magnesium stearate (8.4 g, TAIHEI CHEMICAL INDUSTRIAL CO., LTD.) were measured and mixed.

The obtained mixed powder was tabletted using a tabletting machine (Cleanpress Correct 19KAWC, KIKUSUI SEISAKUSHO LTD.) and 10 mm$_\phi$ punch having a beveled edge at compression pressure 9.9 (kN/cm$^2$) to give tablets each weighing 420 mg.

The obtained tablets were subjected to a dissolution test at pH 2.0 (KCl/HCl buffer), 900 mL, 50 rpm (Paddle Method). As a result, 101% of pioglitazone hydrochloride was eluted in 15 min.

The obtained tablets were subjected to a dissolution test at pH 2.0 (KCl/HCl buffer), 900 mL, 50 rpm (Paddle Method) after preservation for 6 months at temperature 40° C./humidity 44%. As a result, 87% of pioglitazone hydrochloride was eluted in 15 min.

Example 8

Coated particle L (500 g) produced in Comparative Example 1 was charged in a tumbling fluidized bed granulating-coating machine (MP-10, POWREX CORPORATION), and a dispersion of Eudragit E100 (54.6 g, Degussa Japan Co., Ltd.) in polyethylene glycol (27.3 g, Sanyo Chemical Industries, Ltd.), ethanol (532.5 g) and water (532.5 g) was sprayed thereon to give coated particle J.

Coated particle J (7.1 g), sized powder B (12.11 g) obtained in Example 2, crystalline cellulose (1.05 g, CEOLUS KG-802, Asahi Kasei Chemicals Corporation), crospovidone (0.53 g, Polyplasdone XL-10, ISP JAPAN LTD.) and magnesium stearate (0.21 g, TAIHEI CHEMICAL INDUSTRIAL CO., LTD.) were measured and mixed.

The obtained mixed powder was tabletted using Auto-graph (AG-1, Shimadzu Corporation) and 10 mm$_\phi$ punch having a beveled edge at compression pressure 11 (kN/cm$^2$) to give tablets each weighing 420 mg.

The hardness of the obtained tablets was measured with a hardness meter (Toyama Sangyo Co., Ltd.) and found to be 31.3(N) (n=3).

Example 9

Coated particle L (500 g) produced in Comparative Example 1 was charged in a tumbling fluidized bed granulating-coating machine (MP-10, POWREX CORPORATION), and a dispersion of Eudragit E100 (54.6 g, Degussa Japan Co., Ltd.) in talc (27.3 g, Matsumurasangyo Co., Ltd.), ethanol (532.5 g) and water (532.5 g) was sprayed thereon to give coated particle K.

Coated particle K (7.1 g), sized powder B (12.11 g) obtained in Example 2, crystalline cellulose (1.05 g, CEOLUS KG-802, Asahi Kasei Chemicals Corporation), crospovidone (0.53 g, Polyplasdone XL-10, ISP JAPAN LTD.) and magnesium stearate (0.21 g, TAIHEI CHEMICAL INDUSTRIAL CO., LTD.) were measured and mixed.

The obtained mixed powder was tabletted using Auto-graph (AG-1, Shimadzu Corporation) and 10 mm$_\phi$ flat punch having a beveled edge at compression pressure 11 (kN/cm$^2$) to give tablets each weighing 420 mg.

Example 10

Pioglitazone hydrochloride (663.2 g), Eudragit E PO (180 g, Degussa Japan Co., Ltd.) and lactose (416.8 g, MEGGLE JAPAN CO., LTD.) were measured, and dissolved and dispersed in ethanol (2320 g) and water (1880 g) to give a dispersion.

Lactose-crystalline cellulose spherical granules (1200 g, Nonpareil 105T, Freund Corporation) were charged in a tumbling fluidized bed granulating-coating machine (MP-10, POWREX CORPORATION) and the above-mentioned dispersion was sprayed thereon to give coated particle N. In the same manner as above, twice amount of coated particle N was obtained.

Mannitol (3732 g, PEARTOL mannitol (trade name), ROQUETTE JAPAN K.K.), crystalline cellulose (519.8 g, CEOLUS KG-802, Asahi Kasei Chemicals Corporation), crospovidone (346.5 g, Kollidon CL-F, BASF JAPAN LTD.) and aspartame (165 g, Ajinomoto Co., Inc.) were charged in a fluidized bed granulating machine (FD-5S, POWREX CORPORATION) and granulated with a dispersion of mannitol (82.5 g, PEARTOL mannitol (trade name), ROQUETTE JAPAN K.K.) and yellow ferric oxide (1.82 g, manufactured by Ansted) in water (990 g) to give granulation powder P. In the same manner as above, twice amount of granulation powder P was obtained.

Coated particle N (2706 g), granulation powder P (6464 g) and magnesium stearate (70.4 g, TAIHEI CHEMICAL INDUSTRIAL CO., LTD.) were mixed to give a mixed powder Q.

The mixed powder was tabletted using a tableting machine (Aquarius, KIKUSUI SEISAKUSHO LTD.) and 10 mm$_\phi$ punch having a beveled edge at compression pressure 7.4 (kN/cm$^2$) to give tablets each weighing 420 mg.

The obtained tablets were subjected to a dissolution test at pH 2.0 (KCl/HCl buffer), 900 mL, 50 rpm (Paddle Method). As a result, 100% of pioglitazone hydrochloride was eluted in 15 min.

Example 11

The mixed powder Q obtained in Example 10 was tabletted using Auto-graph (AG-1, Shimadzu Corporation) and 8 mm$_\phi$ punch having a beveled edge (with a score line) at compression pressure 5 (kN/cm²) to give tablets each weighing 210 mg.

Example 12

The mixed powder Q obtained in Example 10 was tabletted using Auto-graph (AG-1, Shimadzu Corporation) and a flat punch (long diameter 14 mm, short diameter 9 mm) at compression pressure 13 (kN/cm²) to give tablets each weighing 630 mg.

Experimental Example 1

The disintegration time of the tablets obtained in the Examples in the oral cavity was measured.

The time necessary for a tablet to completely dissolved without chewing at all in the mouth of a healthy subject was taken as the oral cavity disintegration time (n=1 or 3). The results are shown in Table 1. In the Table, the oral cavity disintegration time of Examples 1-5 and 7 is the value of n=1, and the oral cavity disintegration time of Examples 6 and 8-10 is the average value of n=3.

TABLE 1

|  | oral cavity disintegration time (sec) |
|---|---|
| Example 1 | 15 |
| Example 2 | 25 |
| Example 3 | 42 |
| Example 4 | 84 |
| Example 5 | 74 |
| Example 6 | 23.7 |
| Example 7 | 47 |
| Example 8 | 53.3 |
| Example 9 | 33.3 |
| Example 10 | 29.3 |

Experimental Example 2

The tablets obtained in Comparative Examples and Examples were evaluated for the unpleasant taste of pioglitazone or a salt thereof (bitter taste) by a sensory test using healthy subjects.

The bitter taste was evaluated based on the following criteria.
1. bitter taste was not felt
2. bitter taste was hardly felt
3. bitter taste was felt but could be endured
4. bitter taste was too much to be kept in mouth The results are shown in Table 2. In the Table, the bitter taste of Comparative Example 2, Examples 1-5 and 7 is the value of n=1, and the bitter taste of Comparative Example 1, Examples 6 and 8-10 is the average value of n=3.

TABLE 2

|  | bitter taste |
|---|---|
| Comparative Example 1 | 3.3 |
| Comparative Example 2 | 4 |
| Example 1 | 1 |
| Example 2 | 1 |
| Example 3 | 1 |
| Example 4 | 1 |
| Example 5 | 1 |
| Example 6 | 1 |
| Example 7 | 1 |
| Example 8 | 1.7 |
| Example 9 | 1.3 |
| Example 10 | 1 |

As is clear from Table 2, the tablet of the present invention remarkably masks the unpleasant taste (bitter taste) of pioglitazone and a salt thereof as compared to the tablets of Comparative Examples 1 and 2. In other words, by a combined use of pioglitazone or a salt thereof and an acid-soluble polymer, the unpleasant taste (bitter taste) of pioglitazone and a salt thereof can be remarkably masked.

INDUSTRIAL APPLICABILITY

The solid preparation of the present invention can be administered very easily since the unpleasant taste of pioglitazone or a salt thereof is sufficiently masked, and therefore, is useful as a pharmaceutical product with high administration compliance of patients. When the solid preparation of the present invention is a solid preparation rapidly disintegrating in the oral cavity, the solid preparation is extremely useful as a pharmaceutical product with high administration compliance of patients having difficulty in swallowing pharmaceutical agents, such as the elderly and children, and the like, since the unpleasant taste of pioglitazone or a salt thereof is sufficiently masked and the preparation has superior disintegration property in the oral cavity. Moreover, the solid preparation rapidly disintegrating in the oral cavity shows superior properties of appropriate preparation strength, long-term preservation stability and the like.

This application is based on application No. 2006-124456 filed in Japan, the contents of which are incorporated hereinto by reference.

The invention claimed is:

1. A solid preparation comprising particles comprising (i) core particles consisting of one or more excipients, and (ii) pioglitazone or a salt thereof and an acid-soluble polymer both coating the core particles, wherein the particle size of the core particles is 50 to 500 μm, and the acid-soluble polymer is selected from the group consisting of aminoalkylmethacrylate copolymer F and polyvinylacetal diethylaminoacetate, wherein the solid preparation disintegrates in the oral cavity in 5 to 90 seconds.

2. The preparation of claim 1, wherein the pioglitazone or a salt thereof pioglitazone hydrochloride.

3. The preparation of claim 1, comprising particles wherein the core particles consisting of one or more excipients are coated with (i) a coating layer comprising the pioglitazone or a salt thereof, and (ii) a coating layer comprising the acid-soluble polymer, wherein said coating layer (ii) is formed on said coating layer (i).

4. The preparation of claim 1, comprising particles wherein the core particles consisting of one or more excipients are coated with a coating layer comprising the pioglitazone or a salt thereof and the acid-soluble polymer.

5. The preparation of claim 1, further comprising a saccharide.

6. The preparation of claim 1, further comprising a disintegrant.

7. The preparation of claim 1, further comprising crystalline cellulose.

8. The preparation of claim 1, further comprising a sweetener.

9. The preparation of claim 1, wherein the particle size of the core particle is 100 to 300 μm.

10. A solid preparation comprising particles comprising (i) core particles consisting essentially of one or more excipients, and (ii) pioglitazone or a salt thereof and an acid-soluble polymer both coating the core particles, wherein the particle size of the core particles is 50 to 500 μm, wherein the core particles are pharmacologically inactive, and the acid-soluble polymer is selected from the group consisting of aminoalkylmethacrylate copolymer E and polyvinylacetal diethylaminoacetate wherein the solid preparation disintegrates in the oral cavity in 5 to 90 seconds.

* * * * *

UNITED STATES PATENT AND TRADEMARK OFFICE
CERTIFICATE OF CORRECTION

PATENT NO.       : 8,632,808 B2                                      Page 1 of 1
APPLICATION NO.  : 12/298418
DATED            : January 21, 2014
INVENTOR(S)      : Okochi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 619 days.

Signed and Sealed this
Twenty-second Day of September, 2015

Michelle K. Lee
*Director of the United States Patent and Trademark Office*